US009827194B2

(12) United States Patent
Romanhole et al.

(10) Patent No.: US 9,827,194 B2
(45) Date of Patent: Nov. 28, 2017

(54) SURFACTANT-FREE OIL-IN-WATER TYPE EMULSION, PROCESS FOR PREPARATION THEREOF AND ITS USES

(75) Inventors: Rodrigo Collina Romanhole, Mooca (BR); Leda Fernanda de Jesus, São Paulo (BR); Debora Midori Myaki Pedroso, São Paulo (BR); Valeria Maria Di Mambro, Curitiba (BR); Elisangela Gama, Sao Paulo (BR); Eduardo Alexandre de Oliveria Reis, Sao Paulo (BR); Rodrigo Fuscelli Pytel, Sao Paulo (BR); Kassandra Azevedo Tadini, Sao Paulo (BR); Joice Panzarin Savietto, Sao Paulo (BR)

(73) Assignee: Natura Cosmeticos S.A., Itapecerica da Serra (BR)

( * ) Notice: Subject to any disclaimer, the term of this patent is extended or adjusted under 35 U.S.C. 154(b) by 0 days.

(21) Appl. No.: 13/813,342

(22) PCT Filed: Jul. 29, 2011

(86) PCT No.: PCT/BR2011/000252
§ 371 (c)(1),
(2), (4) Date: May 13, 2013

(87) PCT Pub. No.: WO2012/012857
PCT Pub. Date: Feb. 2, 2012

(65) Prior Publication Data
US 2013/0224133 A1    Aug. 29, 2013

(30) Foreign Application Priority Data

Jul. 30, 2010 (FR) ...................... 10 56309

(51) Int. Cl.
| | | |
|---|---|---|
| A61K 8/00 | (2006.01) | |
| A61K 8/06 | (2006.01) | |
| A61K 9/107 | (2006.01) | |
| A61K 8/19 | (2006.01) | |
| A61K 8/81 | (2006.01) | |
| A61Q 19/00 | (2006.01) | |
| B01F 17/00 | (2006.01) | |

(52) U.S. Cl.
CPC .............. *A61K 9/107* (2013.01); *A61K 8/062* (2013.01); *A61K 8/19* (2013.01); *A61K 8/8147* (2013.01); *A61K 8/8152* (2013.01); *A61Q 19/00* (2013.01); *A61Q 19/005* (2013.01); *B01F 17/0028* (2013.01); *A61K 2800/33* (2013.01); *A61K 2800/72* (2013.01)

(58) Field of Classification Search
CPC .......... A61K 8/97; A61K 31/426; A61K 8/64; A61K 8/498; A61K 8/49; A61K 31/11; A61K 8/345; A61K 8/37
See application file for complete search history.

(56) References Cited

U.S. PATENT DOCUMENTS

| | | |
|---|---|---|
| 5,637,291 A | 6/1997 | Bara et al. |
| 6,534,071 B1 | 3/2003 | Tournilhac et al. |
| 2003/0124158 A1 | 7/2003 | Heidenfelder et al. |
| 2007/0178057 A1 | 8/2007 | SenGupta et al. |
| 2008/0226616 A1 | 9/2008 | Schulz et al. |

FOREIGN PATENT DOCUMENTS

| | | |
|---|---|---|
| EP | 1 920 756 A1 | 5/2008 |
| EP | 2 181 695 A2 | 5/2010 |

OTHER PUBLICATIONS

International Search report for Application No. PCT/BR2011/000252 dated Nov. 19, 2012.
*Pemulen TR-1 and Tr-2 Polymeric Emulsifiers, Waterproof Sunscreen Emulsions Prepared With Pemulen Polymers*, Noveon, TDS-232-3 (1995) 3 pages.
*Introducing Pemulen* Polymeric Emulsifiers*, Lubrizol Technical Data Sheet, TDS-114 (2002) 1-7.
IARC, *Re-Evaluation of Some Organic Chemicals, Hydrazine and Hydrogene Peroxide*, IARC Monographs on the Evaluation on Carcinogenic Risks to Humans, V. 71, 1999, p. 432.
Cognis, *Cosmedia SP—an Innovative Polymer for Skin Care Products With High Precision*, Skin Care Forum, Issue 32, Mar. 2003 3 pages.
Idson, B., *Effects of Emulsifiers on Skin*, Cosmetics & Toiletries, v. 106, May 1991, pp. 43-51.
Rieger, M. M. et al., *Surfactants in Cosmetics*, 2. Ed. New York, Marcel Bekker, Inc., 1997, 365 pages.
International Preliminary Report on Patentability and Written Opinion for Application No. PCT/BR2011/000252 dated Feb. 5, 2013.
Office Action for European Application No. EP 11745475.1 dated Jul. 11, 2017, 5 pages.
Montenegro, L. et al., *Effects of Silicone Emulsifiers on in vitro Skin Permeation of Sunscreens From Cosmetic Emulsions*, J. Cosmet. Sci., 55 (Nov./Dec. 2004) 509-518.
Office Action for European Application No. EP 11 745 475.1 dated Sep. 22, 2015.

*Primary Examiner* — Nannette Holloman
(74) *Attorney, Agent, or Firm* — Alston & Bird LLP

(57) ABSTRACT

There is described an oil-in-water emulsion free of surfactant agents comprising: A) At least a cross-polymer acrylate/alkyl-acrylate or derivatives thereof, or mixtures thereof in the aqueous phase of the emulsion; b) At least a polyacrylate or derivatives thereof, or mixtures thereof in the oily phase of the emulsion, and c) At least a neutralizing agent. Further, the present invention refers to a process of obtaining a surfactant-free emulsion and its use in cosmetics and pharmaceuticals compositions. The emulsion in question can be applied to all kinds of skin, being also indicated for people with sensitive skin.

10 Claims, No Drawings

SURFACTANT-FREE OIL-IN-WATER TYPE EMULSION, PROCESS FOR PREPARATION THEREOF AND ITS USES

The present invention refers to a surfactant-free oil-in-water (O/W) type emulsion which can be destined, particularly, for application on sensitive skin since it has no surfactants.

DESCRIPTION OF THE STATE OF THE ART

Surfactants are amphiphilic molecules widely used in the cosmetics and pharmaceutical fields due to their capacity to interact with the various phases of a composition, modifying its structure and altering physical and chemical parameters, such as stability rheology and appearance.

This capacity to interact results in a vast gamut of benefits and desirable functions for the cosmetics industry, namely the capacity of detergency, wetting, solubilization, foaming, dispersion of particles and use as emulsifying agent (Rieger & Rhein, 1997).

The use of surfactants, more particularly as emulsifying agent, is broadly exploited in the cosmetics industry in skin creams and lotions, sun protectors, among others, providing homogeneous and stable emulsions.

However, the use of surfactants has certain drawbacks. It is known that surfactants can interact with the skin in many ways, acting on the surface of the stratum corneum and can even penetrate into deeper cutaneous layers. Depending on its emulsification capacity, the surfactant may damage the cutaneous barrier causing loss of water and facilitating permeabilization of undesirable chemical substances. Additionally, there is the possibility of losing low molecular weight hydrophilic components which play an important role in maintaining skin flexibility (Idson, 1991).

As a result, the topical application of cosmetic products containing surfactants that may cause skin damage such as drying, roughness and flaking, and may cause inflammation symptoms, such as redness and swelling (Idson, 1991).

The surfactants' potential for irritability is particularly undesirable for sensitive skin.

Sensitive skin is that which tends to become irritated or suffer an allergic reaction due to internal and external factors. On sensitive skin, the adverse skin reactions when in contact with one of these factors is more intense and frequent compared to the average, and may present symptoms of redness, burning, itching, marking, among others. People with this kind of skin generally seek anti-allergenic dermatological products or with low irritative potential. In light of the irritability potential of surfactants, developing dermatological formulations free of surfactants would be particularly beneficial for people with this kind of skin.

In order to solve the problems set forth herein, the present invention refers to an emulsion comprising a simple combination of just two polymers which dispenses with the use of surfactants as emulsifying agents. As a result of this combination, a homogenous and stable emulsion was obtained, having low irritability and low allergenic potential, which may be indicated for sensitive skin. Further, as an additional benefit, the absence of surfactants and presence of polymers increases the active ingredients' resistance to water on the skin, particularly sun screens. Additionally, the present invention dispenses with the addition of preservatives which makes it ideal for sensitive skin including baby skin.

In the state of the art, can be found some surfactant-free formulations such as emulsifying agents to solve the problem of skin irritability. In this sense, we cite document U.S. Pat. No. 6,534,071 which discloses a composition in the form of an oil-in-water (O/W) emulsion containing an oily phase dispersed in aqueous phase. This emulsion does not contain surfactants, but specific-sized cellulose fibers and can be applied to dry and/or sensitive skin.

Document EP 1 920 756 discloses a water-based cosmetic matrix destined for the preparation of surfactant-free cosmetic formulations. Said water-based matrix comprises at least a vegetable ester of glycerin containing one or more polyunsaturated fatty acids, at least a sequestering agent (chelation), at least an antioxidant agent and at least an unsaponifiable fraction of an oil or natural butter. This document describes that said cosmetic matrix does not contain preservatives and contains a cosmetic base in the form of cream for sensitive skin and treatment of wrinkles.

U.S. Pat. No. 5,637,291 discloses a surfactant-free emulsion that presents an oily phase in a gelled aqueous phase. This composition comprises oil, water, at least a gelling agent and expanded hollow thermoplastic particles of acrylonitrile polymer or copolymer. Among the options of gelling agents that can be used, the polyacrylates and natural gums are cited, among others. It is known that acrylonitrile is irritating to the skin and presents relative carcinogenic potential. According to the International Agency for Cancer Research (IARC), acrylotrile is a potentially carcinogenic compound, and tests on animals have provided sufficient evidence that exposure to acrylonitrile increases the incidence of tumoral cells. (IARC, 1999). Moreover, differently to the oil-in-water emulsion object of the present invention, the thermoplastic polymer particles and the gelling agents are dispersed in aqueous phase, primarily in the addition of the oily phase in the system; while in the oil-in-water emulsion object of this invention, the cross-polymer and the polyacrylate are dispersed in separate phases of the emulsion to achieve a preferred and specific degree of viscosity.

Therefore, based on the following description of the present invention, it can be concluded that the state of the art does not include surfactant-free oil-in-water emulsions that are stabilized solely by a combination between two polymeric components, with suitable stability and reduced or no irritability.

OBJECTIVES OF THE INVENTION

The objective of the present invention is to provide a surfactant-free oil-in-water (O/W) type emulsion, that presents stability, low allergenic potential, reduced or no irritability and suitable sensation for cosmetics and pharmaceutical products.

Further, the objective of the present invention is to provide a surfactant-free oil-in-water emulsion indicated for individuals with sensitive skin.

BRIEF DESCRIPTION OF THE INVENTION

The object of the invention is an oil-in-water emulsion comprising:
a) At least a acrylate/alkyl-acrylate cross-polymer or derivatives thereof, or mixtures thereof in the aqueous phase of the emulsion; and
b) At least a polyacrylate or derivatives thereof, or mixtures thereof in the oily phase of the emulsion,
c) At least a neutralizing agent,
being free of surfactants.

DETAILED DESCRIPTION OF THE INVENTION

The invention refers to an oil-in-water (O/W) type emulsion comprising:
a) At least a acrylate/alkyl-acrylate cross-polymer or derivatives thereof, or mixtures thereof in the aqueous phase of the emulsion; and
b) At least a polyacrylate or derivatives thereof, or mixtures thereof in the oily phase of the emulsion,
c) At least a neutralizing agent,
being free of surfactants.

According to a preferred embodiment, the present invention refers to an oil-in-water emulsion comprising:
a) of about 0.05 to about 5.00% of at least a acrylate/alkyl-acrylate cross-polymer or derivatives thereof, or mixtures thereof in the aqueous phase of the emulsion; and
b) of about 0.1 to about 10.0% of a polyacrylate or derivatives thereof, or mixtures thereof in the oily phase of the emulsion; and all the percentages are based on the total mass of the composition.
c) at least a neutralizing agent in a sufficient quantity that results in a pH value of about 6;
being free of surfactants.

In an even more preferred embodiment of the present invention, the surfactant-free oil-in-water emulsion comprises of about 0.15 to about 0.25% in mass of at least a acrylate/alkyl-acrylate cross-polymer or derivatives thereof, or mixtures thereof and of about 1 to about 2% in mass of a polyacrylate or derivatives thereof, or mixtures thereof and these percentages are calculated based on the total mass of the formulation.

a) Acrylate/Alkyl-Acrylate Cross-Polymer

Among the options of acrylate/alkyl-acrylate cross-polymers that can be added to the emulsion object of this invention are: acrylate/C10-30 alkyl-acrylate cross-polymer, poly C10-30 alkyl-acrylate, Potassium acrylate/C10-30 alkyl-acrylate cross-polymer, Sodium acrylate/C10-30 alkyl acrylate cross-polymer.

Preferably, the acrylate/alkyl-acrylate cross-polymer to be added to the emulsion in question is the acrylate/C10-30 alkyl-acrylate cross-polymer.

The acrylate/alkyl-acrylate cross-polymer to be added to the emulsion should basically be a hydrosoluble polymer, which may also present high dispersibility in the oily phase of the emulsion.

Essentially, the acrylate/C10-30 alkyl-acrylate cross-polymer acts like an emulsifying polymer of the formulation and is a component that is compatible with most of the cosmetic adjuvants usually employed in emulsion, such as oils and emollient esters and co-solvents, film-forming and wetting agents, preservatives, chelating agents and antioxidants, fragrances, colorings and even low HLB value surfactants.

The acrylate/alkyl-acrylate cross-polymer should be present in the aqueous phase of the oil-in-water emulsion free of emulsifying agents.

Commercially, the acrylate/C10-30 alkyl-acrylate cross-polymer can be found under the name "Permulen® TR1 or TR2" manufactured by the company Noveon—The Specialty Chemical Innovator. The difference between Permulen TR1 and Permulen TR2 consists of the degree of viscosity provided to the final emulsion. Permulen TR1 drift in a more viscous emulsion, having a jellified appearance and Permulen TR2 drift in a more fluid emulsion, less consistent in appearance.

More preferably, the acrylate/alkyl-acrylate cross-polymer to be added to the emulsion in question is Pemulen TR2.

The cross-polymer acrylate/alkyl-acrylate is present in the emulsion presented herein in a quantity that varies between 0.05 to 5% in mass, preferably from 0.15 to 0.25% in mass, based on the total mass of the composition.

b) Polyacrylate

Among the options of polyacrylates that can be added to the emulsion that is the object of this invention are: Potassium Aluminum Polyacrylate, Potassium Polyacrylate, Sodium Polyacrylate, Sodium Polyacrylate Starch, Ammonium Polyacrylate and Glyceryl Polyacrylate.

Preferably, the polyacrylate to be added to the emulsion object of the present invention is sodium polyacrylate. Commercially, said sodium polyacrylate can be found under the name "Cosmedia® SP" manufactured by the company Cognis-carechemicals.

The polyacrylate belongs to the group of polymers and has a broad variety of applications in industry, including use as sequestering agent, consistency agent, and absorption agent in disposable diapers, among others.

The polyacrylate should be present in the oily phase of the oil-in-water emulsion free of emulsifying agents.

The polyacrylate is present in the emulsion presented herein in a quantity that varies between 0.1 to 10% in mass, preferably from 1 to 2% in mass, based on the total mass of the composition.

b) Neutralizing Agent

The neutralizing agent of the present invention can be chosen from the group that comprising triethanolamine, sodium hydroxide, potassium hydroxide and aminomethylpropanol or any other neutralizing agent known on the market that acts in the same way as those already mentioned, as well as mixtures thereof.

The neutralizing agent is present in the emulsion presented herein in a sufficient quantity to adjust the pH value to about 6.

c) Optional Components

The emulsion according to this invention may optionally comprise components usually used in cosmetic or pharmaceutical products according to the application sought for the composition to be prepared. The optional components include: antioxidant agents, preservatives, film formers, microcrystalline web support formers, co-solvent polymeric agents and/or copolymeric agents, denaturants, consistency agents, emollients, wetting and/or moisturizing agents and conditioners, but is not limited to these alone.

In a preferred embodiment of the present invention, the surfactant-free oil-in-water emulsion comprises as optional component, of about 0.05 to about 4% in mass, preferably of about 0.1% to about 0.3% in mass of a hydrophilic polysaccharide, being this percentage calculated based on the total mass of the formulation.

Among the options of hydrophilic polysaccharides that can be present in the emulsion that is the object of the present invention are: gellan gum, xanthan gum, modified xanthan gums and derivatives of modified amides.

Preferably, the hydrosoluble polysaccharide to be added to the emulsion that is the object of this invention is selected from among the group of gums. More specifically, the polysaccharide preferably used in this emulsion is a xanthan gum.

In a preferred embodiment of the present invention, the oil-in-water emulsion free of emulsifying agents comprises, in a physiologically acceptable vehicle, of about 0.05 to about 4.00% in mass, preferably of about 0.1 to about 0.3% in mass of xanthan gum, and this percentage is calculated based on the total mass of the formulation.

Optionally, the present invention further comprises an active ingredient that can be selected, for example, from among the group: sun screens (UV), anti-inflammatory agents, tranquilizers, moisturizers, collagen and elastine synthesis stimulators, anti-microbians, cell renewal agents, among others.

Further, in a preferred embodiment of the present invention, the emulsion is free of preservatives, which renders the irritability potential even lower, being particularly indicated for sensitive skin for this reason also.

By means of the combination between the acrylate/alkyl-acrylate cross-polymer, polyacrylate and, optionally, xanthan gum, we have developed an emulsion without the need to use surfactants. Consequently, the absence of surfactants means the emulsion is less allergenic and less irritating to the skin, which makes it particularly indicated for individuals with sensitive skin.

Further, the optional absence of preservatives of the present invention results in an emulsion with an even lower allergenic and irritating potential, being particularly beneficial for individuals with sensitive skin.

Additionally, the combination between the polymers referred to above provides the emulsion chemical and chemical-physical stability, that is, there is no separation between the phases of the emulsion at rest, nor is there the loss of functionality of the active ingredients eventually added. The use of the polymers separately results in an unstable formulation or with an unsuitable sensation for cosmetic use.

The emulsion according to the present invention presents viscosity and sensation suitable for cosmetic and pharmaceutical use.

Examples of galenic forms for the use of surfactant-free emulsions are:

Fluid or semi-solid emulsion, for example:
Body moisturizing milk;
Moisturizing milk for the face;
Body moisturizing lotion;
Moisturizing lotion for the face;
Emulsions for sensitive skin.
Sun screens or blocks for adults or children, whether or not designed for simultaneous use while playing sports;
Body or facial moisturizers;
Anti-signs products for body and face;
Firming products for body and face;
Self-tanning products;
Insect repellant products;
Body or facial skin-lightening moisturizers;
Anti-cellulite products;

A surfactant-free oil-in-water emulsion object of the present invention presents other physical and chemical characteristics that are suitable and safe for the user of this product, such as:

Appropriate texture during application, non-sticky and non-oily;
Good spreadability and glide during application;
Low quantity of oily residue on skin after application;
Low comedogenicity;
Improved skin hydration as it does not remove the skin's hydrolipidic layer;
Better skin compatibility.

Process of Preparing of the Emulsion Object of the Present Invention

To obtain the results of the present invention, it is strictly necessary to following the phases in which the compulsory components should be present in the preparation process, namely: the acrylate/alkyl-acrylate cross-polymer should be added in the aqueous phase of the emulsion and the sodium polyacrylate should be added in the oily phase of the emulsion.

Preferentially, the emulsion production process described here comprises the following steps:

a) Add in a first recipient the acrylate/alkyl-acrylate cross-polymer and, optionally, a xanthan gum in the aqueous phase of the emulsion and stir with rotation at about 2500 rpm, while heating, until the temperature reaches 75° C. to 85° C. (about 10 min.);

b) Separately, in a second recipient, stir with maximum rotation of 2500 rpm the oily phase of the emulsion, including the polyacrylate, while heating until the temperature reaches 75° C. to 85° C. (about 10 min.);

c) When both phases are at a temperature of 75° C. to 85° C., pour the contents of the second recipient (the oily phase) into the first recipient (the aqueous phase) and stir with rotation at about 2500 rpm for about 10 minutes, keeping the temperature between 75° C. and 85° C.;

d) After concluding step c), begin cooling, keeping the system under stirring at about 2500 rpm;

d') Optionally, add adjuvants when the system reaches a temperature between 50° and 55° C. under stirring at about 3000 rpm;

e) Add neutralizing agents when the temperature of the cooled system obtained in d) reaches 40° to 45° C. under stirring at about 3000 rpm;

f) Cool the system to about 35° C. under stirring at about 3000 rpm.

Said stirring is preferably obtained by means of a reactor which may be one commonly used in the industry, preferably a turbine reactor, more preferably the reactor used is a Koruma™ reactor.

It is important to underline that the combination between acrylate/alkyl-acrylate cross-polymer and sodium polyacrylate is absolutely necessary to obtain the results presented herein.

The results achieved in the present invention are not achieved by using singly polymers. The use of polyacrylate alone, for example, results in an unstable formulation, whereas the use of acrylate/alkyl-acrylate cross-polymer alone gives the formulation a gelatinous consistency or extremely fluid, depending on the concentration in which the polymer is used. Accordingly, the use of singly polymers results in an unsuitable formulation for cosmetic products due to their instability and unattractive consistency.

It must also be highlighted that it is fundamental that the polymers be added in the specific phases described in the present invention, that is to say, the acrylate/alkyl-acrylate cross-polymer should be added in the aqueous phase and the polyacrylate should be added in the oily phase of the emulsion. Reversing the phases or adding the polymers together in the same phase results in an unstable emulsion.

EXAMPLES

Table 1 shows an example of the sunscreen emulsion O/W type free of surfactants prepared according to the present invention:

TABLE 1

Example of cosmetic composition

| INCI name | Function | Concentration (% in mass) |
|---|---|---|
| WATER | QSP | Qsp |
| ACRYLATES/C10-30 ALKYL ACRYLATE CROSSPOLYMER | Consistency Agent | 0.10 |
| CYCLOPENTASILOXANE | Emollient | 10.00 |
| CYCLOPENTASILOXANE/ DIMETHICONE CROSSPOLYMER | Emollient | 5.00 |
| DICAPRYLYL CARBONATE | Emollient | 5.00 |
| DISODIUM EDTA | Chelating Agent | 0.05 |
| GLICERET-26 | Wetting Agent | 6.00 |
| SODIUM HIDROXIDE | Neutralizing Agent | 0.01 |
| ISONONYL ISONONANOATE | Emollient | 4.00 |
| ASTROCARYUM MURUMURU BUTTER | Emollient | 0.50 |
| C12-C15 ALKYL BENZOATE | Emollient | 3.00 |
| XANTHAN GUM | Consistency Agent | 0.10 |
| THEOBROMA GRANDIFLORUM SEED BUTTER | Emollient | 0.50 |
| GLICERIN | Wetting Agent | 5.00 |
| PENTYLENE GLYCOL | Wetting Agent | 5.00 |
| ETHYLHEXYLGLYCERIN | Emollient | 5.00 |
| SODIUM POLYACRYLATE | Consistency Agent | 1.00 |

Example 2

Clinical Evaluation of Cutaneous Tolerance to Cosmetic Compositions Containing the Emulsion of the Present Invention after Repeated Applications The aim of this evaluation was to verify the cutaneous compatibility and the absence of sensations of discomfort after 5 consecutive applications under controlled conditions of a product having the following composition:

Selected volunteers were evaluated by a dermatologist to check their skin conditions to take part in this study. Subsequently, on 12 (twelve) volunteers considered apt to participate in the test, a skin area of 40 cm² was sectioned in indelible ink on the right forearm of each volunteer taking part in the study.

The product was applied in a uniform manner on said sectioned area twice per day for four days running: the first application of the day was performed at a clinic and the second at the home of each volunteer. On the fifth day after the start of the test, a single application was made. The applications made at the clinic had the following procedure: the product was applied to the marked region and the arm remained flexed for 15 minutes and extended for 30 consecutive minutes. In the home application, the volunteers were advised to apply the product and keep their arm in a normal position for 60 minutes and note down any sensation of discomfort.

After 24, 48, 72 and 96 hours from the start of the study, the volunteers returned to the clinic for a reading of the region, a new application and a new reading. On the fifth day (120 hours after the start of the study) the volunteers returned to the clinic for the last application of the product and final evaluation.

Before taking the readings, the volunteers were advised to remove the product with plenty of water. The readings were carried out and noted down, and the data collected was tabulated as shown below. Additionally, after the final stage of the schedule of applications of the product the volunteers underwent a further dermatological evaluation which compared the volunteers' initial skin conditions before taking part in the study with the conditions presented at the end of the test.

Results:

Interpreting the results was based on the cutaneous evaluation and the recording of the sensations of discomfort during the application of the product. The results were tabulated and determined based on the calculation of the ratio of reactive volunteers with the total number of volunteers who concluded the study. The cutaneous compatibility of the product was considered very good, good, moderate or bad, according to the following scale:

TABLE 2

Cutaneous Compatibility Classification

| Cutaneous Compatibility | Percentage of volunteers displaying clinical signs attributed to the test product | Percentage of volunteers feeling sensations of discomfort attributed to the test product |
|---|---|---|
| Very good | 0 | 0 |
| Good | 0 | <30 |
| Moderate | <20 | +/− |
|  | 0 | 30 to 50 |
| Bad | ≥20 | Presence or absence |
|  | 0 | 50 |

Very good: absence of clinical signs or sensations of discomfort;

Good: absence of local clinical signs but with some sensation of discomfort in less than 30% of the volunteers;

Moderate: presence of clinical signs in at least 20% of the volunteers, with or without sensation or discomfort or sensation of discomfort felt by 30-50% of the volunteers;

Bad: presence of clinical signs on 20% of the volunteers, with or without sensation of discomfort or sensation of discomfort felt by 30-50% of the volunteers.

Results:

TABLE 3

Data from the evaluation of the clinical signs

| Vol | Days of Study | | | | |
|---|---|---|---|---|---|
|  | 1 | 2 | 3 | 4 | 5 |
| 1 | − | − | − | − | − |
| 2 | − | − | − | − | − |
| 3 | − | − | − | − | − |
| 4 | − | − | − | − | − |
| 5 | − | − | − | − | − |
| 6 | − | − | − | − | − |
| 7 | − | − | − | − | − |
| 8 | − | − | − | − | − |
| 9 | − | − | − | − | − |
| 10 | − | − | − | − | − |
| 11 | − | − | − | − | − |
| 12 | − | − | − | − | − |
| Total frequency of appearances (sum) per day | | | | | |
| Total | 0 | 0 | 0 | 0 | 0 |
| Positive (+) | 0 | 0 | 0 | 0 | 0 |
| Positive (++) | 0 | 0 | 0 | 0 | 0 |
| Positive (+++) | 0 | 0 | 0 | 0 | 0 |

Negative (−) = Injury absent

Positive (+) = Light erythema (hardly perceptible, with undefined edges and without edema)

Positive (++) = Clear erythema (definable with clear edges, delimited and associated to edema)

Positive (+++) = Erythema + edema + papules/vesicles

TABLE 4

Descriptions of discomfort detected at Clinic

| Vol | Days of Use | | | |
|---|---|---|---|---|
| | 1 | 2 | 3 | 4 |
| 1 | 0 | 0 | 0 | 0 |
| 2 | 0 | 0 | 0 | 0 |
| 3 | 0 | 0 | 0 | 0 |
| 4 | 0 | 0 | 0 | 0 |
| 5 | 0 | 0 | 0 | 0 |
| 6 | 0 | 0 | 0 | 0 |
| 7 | 0 | 0 | 0 | 0 |
| 8 | 0 | 0 | 0 | 0 |
| 9 | 0 | 0 | 0 | 0 |
| 10 | 0 | 0 | 0 | 0 |
| 11 | 0 | 0 | 0 | 0 |
| 12 | 0 | 0 | 0 | 0 |

TABLE 5

Descriptions of discomfort detected at home

| Vol | Days of Use | | | |
|---|---|---|---|---|
| | 1 | 2 | 3 | 4 |
| 1 | 0 | 0 | 0 | 0 |
| 2 | 0 | 0 | 0 | 0 |
| 3 | 0 | 0 | 0 | 0 |
| 4 | 0 | 0 | 0 | 0 |
| 5 | 0 | 0 | 0 | 0 |
| 6 | 0 | 0 | 0 | 0 |
| 7 | 0 | 0 | 0 | 0 |
| 8 | 0 | 0 | 0 | 0 |
| 9 | 0 | 0 | 0 | 0 |
| 10 | 0 | 0 | 0 | 0 |
| 11 | 0 | 0 | 0 | 0 |
| 12 | 0 | 0 | 0 | 0 |

The following concepts were taken into account upon filling out the tables:

| Group | Compatible descriptions |
|---|---|
| — | None |
| 1 | Burning sensation; local heat |
| 2 | Itching; irritation |
| 3 | Pins and needles; tingling |
| 4 | Burning accompanied by itching |
| 5 | Burning accompanied by tingling |
| 6 | Itching accompanied by tingling |
| 7 | Burning with itching and tingling |
| 8 | Other - |
| Subgroup A | The sensation is transient, lasts some minutes, but then goes away (only mark subgroup when there is discomfort). |
| Subgroup B | The sensation lasts for over 15 minutes. |
| Subgroup X | The intensity of the sensation is light. |
| Subgroup Y | The intensity of the sensation is moderate or intense. |

The above results can be summarized as follows:

| Clinical Signs | Percentage of volunteers displaying clinical signs | Sensations of discomfort | Percentage of volunteers feeling sensations of discomfort |
|---|---|---|---|
| 0 | 0% | 0 | 0% |

Under the conditions in which the product described was evaluated and in the sample of volunteers studied, the data allow the conclusion that the cutaneous compatibility of the product is considered very good.

BIBLIOGRAPHIC REFERENCES

IDSON, Bernard. Effects of Emulsifiers on Skin. Cosmetics & Toiletries, v. 106, p. 43-51, May 1991

RIEGER, Martin M.; RHEIN, Linda D. Surfactants in cosmetics. 2. ed. New York: Marcel Dekker, Inc. 1997

IARC, Re-evaluation of Some Organic Chemicals, Hydrazine and Hydrogene Peroxide, v. 71, p. 43, 1999

The invention claimed is:

1. Oil-in-water emulsion characterized by comprising:
   i) at least an acrylate/alkyl-acrylate cross-polymer, or mixtures thereof in the aqueous phase of the emulsion; and
   ii) at least a polyacrylate, or mixtures thereof in the oily phase of the emulsion,
   iii) at least a neutralizing agent,
   said emulsion being free of surfactants and preservatives.

2. Emulsion according to claim 1, wherein the cross-polymer acrylate/alkyl acrylate cross-polymer can be selected from the group that comprises: acrylate/C10-30 alkyl-acrylate cross-polymer, poly C10-30 alkyl-acrylate, Potassium Acrylates/C10-30 Alkyl Acrylate cross-polymer, Sodium Acrylates/C10-30 Alkyl Acrylate cross-polymer, or derivatives thereof, and mixtures thereof.

3. Emulsion according to claim 2, wherein the acrylate/alkyl acrylate cross-polymer is the acrylate/C10-30 alkyl-acrylate cross-polymer.

4. Emulsion according to claim 1, wherein the polyacrylate is selected from the group that comprises: Potassium Aluminum polyacrylate, Potassium polyacrylate, Sodium polyacrylate, Sodium polyacrylate Starch, Ammonium polyacrylate and Glyceryl polyacrylate, or derivatives thereof, and mixtures thereof.

5. Emulsion according to claim 4, wherein the polyacrylate is sodium polyacrylate.

6. Emulsion according to claim 1, comprising
   a) of about 0.05 to about 5.00% in mass of the acrylate/alkyl-acrylate cross-polymer or derivatives thereof in the aqueous phase of the emulsion; and
   b) of about 0.1 to about 10.0% in mass of the polyacrylate and/or derivatives thereof in the oily phase of the emulsion;
   being all percentages based on the total mass of the composition.

7. Emulsion according to claim 6, comprising:
   a) of about 0.15 to about 0.25% in mass of the acrylate/alkyl-acrylate cross-polymer and/or derivatives thereof and
   b) of about 1 to about 2% in mass of the polyacrylate and/or derivatives thereof,
   being all the percentages calculated based on the total mass of the formulation.

8. Emulsion according to claim 1, wherein the neutralizing agent is selected from the group comprising triethanolamine, sodium hydroxide, potassium hydroxide and aminomethylpropanol and derivatives, and mixtures thereof.

9. Emulsion according to claim 1, wherein the neutralizing agent is present in a sufficient quantity to result in a pH about 6.

10. Emulsion according to claim 1, further comprising a hydrophilic polysaccharide selected from the group that comprises: gellan gum, xanthan gum, modified xanthan gums and derivatives of modified amides.

* * * * *